US011540860B2

(12) United States Patent
Kellner et al.

(10) Patent No.: US 11,540,860 B2
(45) Date of Patent: Jan. 3, 2023

(54) SMOKE COLLECTING TROCAR

(71) Applicant: Buffalo Filter LLC, Lancaster, NY (US)

(72) Inventors: William Kellner, Amherst, NY (US); Gregory Pepe, Lancaster, NY (US); Samantha Bonano, Williamsville, NY (US)

(73) Assignee: Buffalo Filter LLC, Lancaster, NY (US)

( * ) Notice: Subject to any disclaimer, the term of this patent is extended or adjusted under 35 U.S.C. 154(b) by 132 days.

(21) Appl. No.: 16/786,245

(22) Filed: Feb. 10, 2020

(65) Prior Publication Data
US 2020/0170673 A1 Jun. 4, 2020

Related U.S. Application Data

(63) Continuation of application No. 15/492,720, filed on Apr. 20, 2017, now Pat. No. 10,617,444.

(60) Provisional application No. 62/324,963, filed on Apr. 20, 2016.

(51) Int. Cl.
*A61B 17/34* (2006.01)
*A61M 13/00* (2006.01)

(52) U.S. Cl.
CPC ...... *A61B 17/3476* (2013.01); *A61B 17/3421* (2013.01); *A61B 17/3474* (2013.01); *A61M 13/003* (2013.01); *A61M 13/006* (2014.02); *A61B 2218/006* (2013.01); *A61M 2205/3334* (2013.01)

(58) Field of Classification Search
CPC .......... A61B 2218/008; A61B 17/3474; A61B 2218/006; A61M 13/003; A61M 13/00; A61M 13/006
See application file for complete search history.

(56) References Cited

U.S. PATENT DOCUMENTS

| 895,729 A | 8/1908 | Cottrell |
| 2,397,197 A | 3/1946 | Newman |
| 3,416,540 A | 12/1968 | Lidums |
| 2007/0249990 A1* | 10/2007 | Cosmescu ........... A61M 13/003 604/27 |

(Continued)

FOREIGN PATENT DOCUMENTS

WO 2014081783 A1 5/2014

OTHER PUBLICATIONS

PCT International Search Report for PCT/US2017/028657, completed Jul. 3, 2017.

*Primary Examiner* — Emily L Schmidt
(74) *Attorney, Agent, or Firm* — Timothy W. Menasco, Esq.; Harter Secrest & Emery LLP

(57) ABSTRACT

Embodiments of the present disclosure provide an apparatus and method for reducing surgical smoke. An exemplary apparatus includes trocar comprising a tubular hollow body circumscribing a cavity extending through a longitudinal axis of the trocar with a gasket at a first end and an exit port at a second end, the tubular hollow body comprising a first wall circumscribing the cavity and a concentrically spaced apart second wall. The apparatus further includes a first plate operable to maintain an electric charged disposed within the cavity on the first wall, and a second plate operable to maintain an electric charge disposed between the first wall and the spaced apart second wall.

11 Claims, 4 Drawing Sheets

(56) References Cited

U.S. PATENT DOCUMENTS

| | | | |
|---|---|---|---|
| 2012/0067212 A1* | 3/2012 | Warren | A61B 18/00 95/57 |
| 2012/0316510 A1 | 12/2012 | Ott | |
| 2015/0182708 A1 | 7/2015 | Barnard | |
| 2017/0007295 A1* | 1/2017 | Geisz | A61B 17/3421 |
| 2017/0086915 A1* | 3/2017 | Batchelor | A61B 18/14 |

* cited by examiner

SMOKE COLLECTING TROCAR

BACKGROUND OF THE INVENTION

Field of the Invention

The present invention relates generally to smoke evacuation, and, more specifically, to a smoke collecting trocar for smoke evacuation during medical procedures.

Description of Related Art

Surgical smoke and aerosol, or plume, is created in connection with surgery. For example, when laser or electrosurgical energy is delivered to a cell, heat is created. This heat vaporizes the intracellular fluid, which increases the pressure inside the cell and eventually causes the cell membrane to burst. In this example, a plume of smoke containing water vapor is released into the atmosphere of the operating room or doctor's office. At the same time, the heat created may char the protein and other organic matter within the cell, and may cause thermal necrosis in adjacent cells. The charring of cells may also release other harmful contaminants, such as carbonized cell fragments and gaseous hydrocarbons.

Electrostatic smoke precipitators are disclosed in U.S. Pat. No. 895,729 issued to Cottrell; U.S. Pat. No. 2,397,197 issued to Newman; and U.S. Pat. No. 3,416,540 issued to Lidums, which are all hereby incorporated by reference.

BRIEF SUMMARY OF THE INVENTION

In view of the foregoing, it is an object of the present disclosure to provide a method and apparatus for reducing surgical smoke and for removing gas.

A first exemplary embodiment of the present disclosure provides an apparatus for reducing surgical smoke. The apparatus includes trocar comprising a tubular hollow body circumscribing a cavity extending through a longitudinal axis of the trocar with a gasket at a first end and an exit port at a second end, the tubular hollow body comprising a first wall circumscribing the cavity and a concentrically spaced apart second wall. The apparatus further includes a first plate operable to maintain an electric charged disposed within the cavity on the first wall, and a second plate operable to maintain an electric charge disposed between the first wall and the spaced apart second wall.

A second exemplary embodiment of the present disclosure provides an apparatus for reducing surgical smoke. The apparatus includes a trocar comprising a tubular hollow body circumscribing a cavity extending through a longitudinal axis of the trocar with a gasket at a first end and an exit port at a second end, the tubular hollow body maintaining a first plate operable to maintain an electric charged and a second plate operable to maintain an opposite electric charge. The apparatus further comprises an insufflator operable to provide gas to the cavity, a charging controller operable to provide an electric charge to the first plate and the second plate, and a flow meter in fluid connection between the insufflator and the trocar, the flow meter operable to measure a flow of gas from the insufflator to the cavity.

A third exemplary embodiment of the present disclosure provides a method of removing gas. The method includes providing a trocar comprising a tubular hollow body circumscribing a cavity extending through a longitudinal axis of the trocar with a gasket at a first end and an exit port at a second end, the tubular hollow body maintaining a first plate operable to maintain an electric charged and a second plate operable to maintain an opposite electric charge, an insufflator operable to provide gas to the cavity, a charging controller operable to provide an electric charge to the first plate and the second plate, and a flow meter in fluid connection between the insufflator and the trocar, the flow meter operable to measure a flow of gas from the insufflator to the cavity. The method further includes inserting the trocar into a surgical cavity, and electrically charging the first plate and the second plate by the charging controller to ionize particles within the surgical cavity and attract the particles toward one of the first plate and the second plate.

The following will describe embodiments of the present disclosure, but it should be appreciated that the present disclosure is not limited to the described embodiments and various modifications of the invention are possible without departing from the basic principles. The scope of the present disclosure is therefore to be determined solely by the appended claims.

BRIEF DESCRIPTION OF THE SEVERAL VIEWS OF THE DRAWING(S)

DETAILED DESCRIPTION OF THE INVENTION

Figure 1:
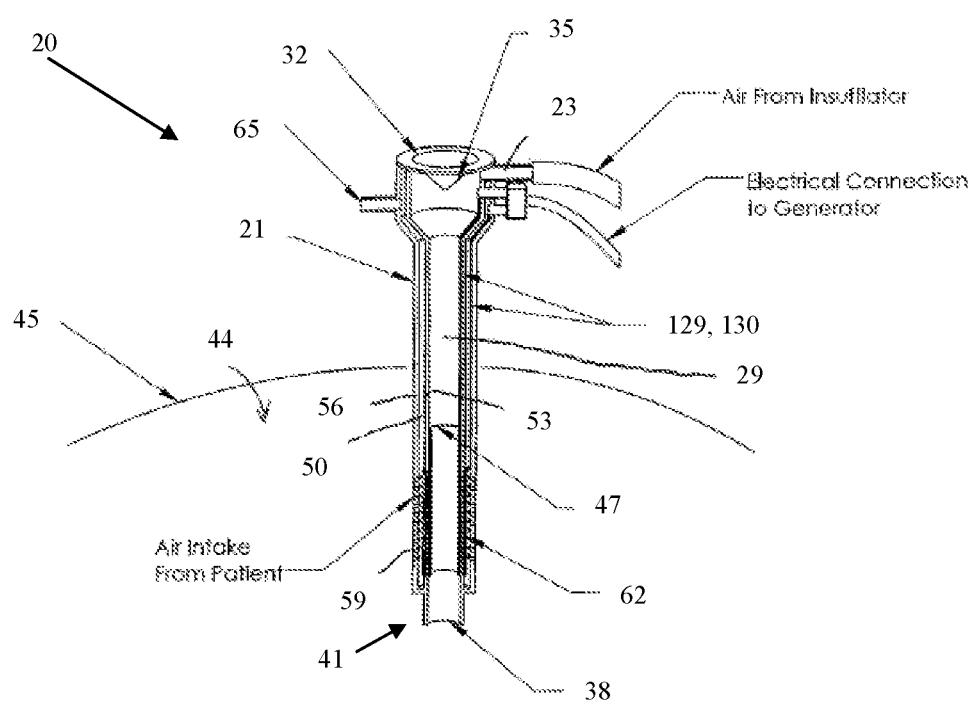
FIG. 1 is a cross-sectional perspective view of a first embodiment of the smoke collecting trocar of the present invention.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, debris, etc.) together with the specification, and are to be considered a portion of the entire written description of this invention. As used in the following description, the terms "horizontal", "vertical", "left", "right", "up" and "down", as well as adjectival and adverbial derivatives thereof, (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or of rotation, as appropriate.

Figure 2:
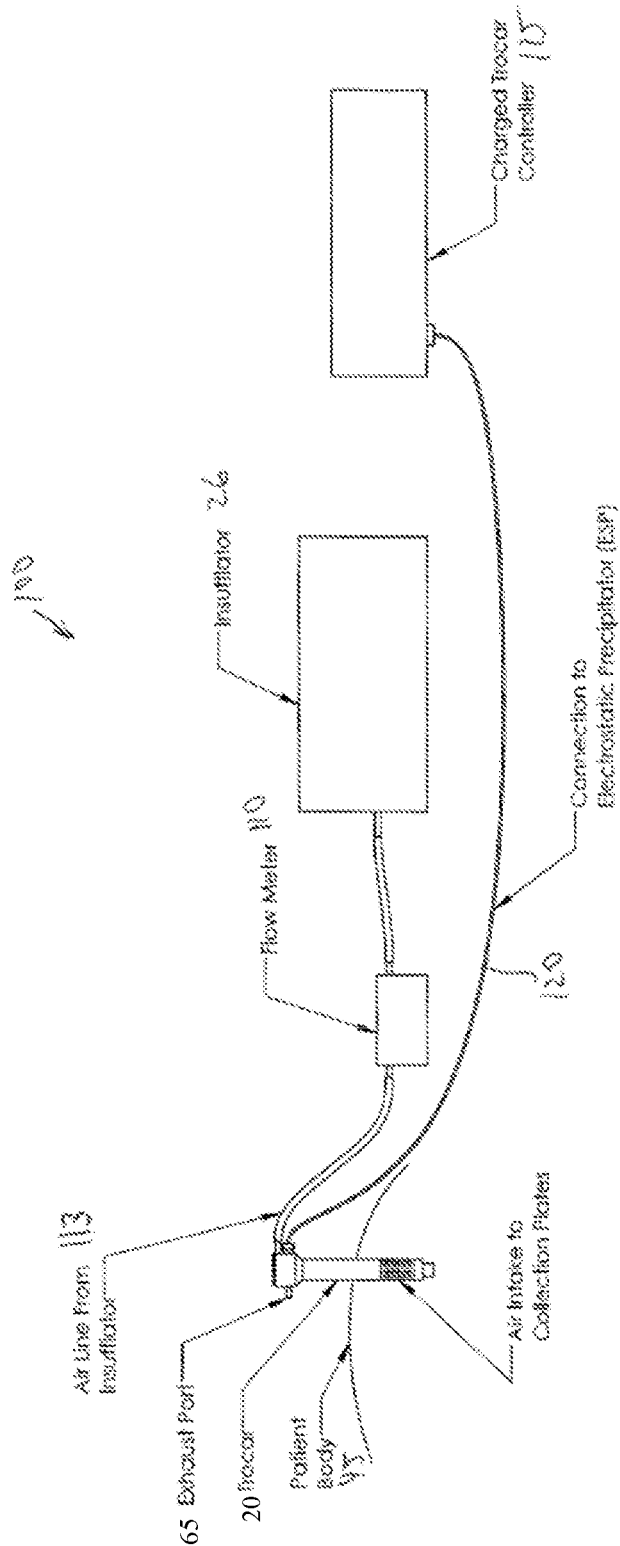
FIG. 2 is a schematic diagram of a system including the smoke collecting trocar of the present invention.
Figure 3:
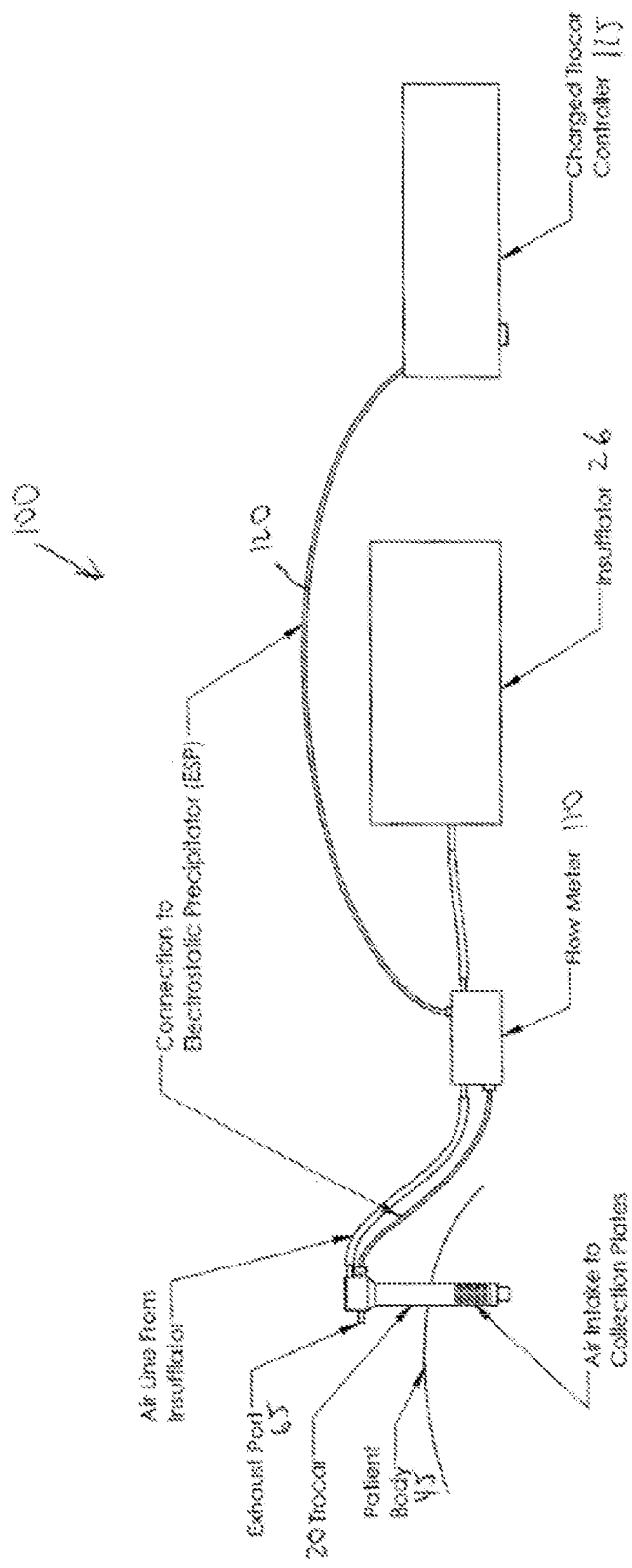
FIG. 3 is a schematic diagram of an alternative embodiment of the system shown in FIG. 2.

Referring now to the drawings, and more particularly to FIG. 1 thereof, a trocar 20 has a body 21 with an inlet 23 for receiving air from an insufflator 26 (FIGS. 2-3). The air passes through a central passageway 29 disposed in the trocar 20. The trocar 20 has a tool entry port 32 with a one way gasket 35 disposed therein. The trocar 20 has a tool exit port 38 at a distal end 41. In use, the trocar 20 is inserted through an incision in a patient to provide a pathway to a cavity 44 inside the body 45 of a patient. The insufflation air and the tool pass through the central passageway to a surgical area inside a cavity 44 of the patient. The insufflation air keeps the cavity 44 pressurized to enlarge the surgical area for a surgical or diagnostic procedure conducted through an entry site established by the trocar 20. Surgical and/or diagnostic tools may be introduced into the cavity 44 through the trocar 20. A scope inserted through the trocar 20 may provide imaging of the area inside the cavity 44. An electrosurgical device may be inserted through the trocar 20 to enable the user to perform a surgical procedure inside the cavity 44. The removal of surgical smoke from the cavity 44 may be desired in the case of electrocautery or electrosurgical procedures that produce surgical smoke.

The air from the insufflator 26 passes through the central passageway 29 in the trocar 20 where it is conveyed through an area that may be surrounded by an ionizer/negative charge plate 47. The incoming air is thereby provided with a negative charge when it enters the cavity 44 to provide an insufflation fluid. When smoke particles are generated by the procedure taking place inside the cavity 44, the negatively charged air in the cavity 44 causes the smoke particles to become negatively charged according to the principles of electrostatic smoke precipitation.

A concentric channel 50 is formed in the trocar 20 and is defined by a wall 53 surrounding the central passageway and an outer wall 56 having a plurality of perforations 59 defined therein. A positively charged collection plate 62 is disposed in the concentric channel 50. The gap between the ionizer/negative charge plate 47 and the collector 62 is tightly controlled to eliminate the possibility of an electrostatic discharge. The arrangement of the plates 4 7 and 62 and the charging of the insufflation air provides an electrostatic smoke precipitator as described below.

During operation, negatively charged smoke particles inside the cavity 44 are drawn from the cavity 44 through the perforations 59 onto the positive collection plate 62 which acts as a smoke collector inside the trocar 20. The smoke particles are removed from the patient and may be disposed of at the end of the procedure through disposal of the trocar 20. Also, the collector plate 62 may be self-cleaning in several ways. The trocar 20 may be capped underneath the collection plate 62 to provide a "particle cup" to receive smoke particles. The charge may be removed from the collector plate 62 and then the plate 62 may be vibrated to remove the particles. Also, the charge may be removed from the collector plate 62 and then a vacuum applied to the area where the plate 62 is located.

This passive smoke removal reduces the need for additional insufflation gas. The benefits include reduced procedural cost, reduced patient temperature loss, and reduced patient tissue dehydration.

The concentric channel 50 is disposed in fluid communication with an air exhaust port 65. If additional smoke evacuation is needed, the air exhaust port 65 may be connected to a vacuum source (not shown).

The two plates 4 7 and 62 may be used to electrically detect the amount of particles on the collector plate 62. This principle would be similar to how a capacitor operates.

Turning to FIG. 2, the entire system 100 is shown with a flow meter 110, the insufflator 26, and a charged trocar controller 115. The flow meter 110 may be disposed between the insufflator 26 and the trocar 20 to measure the flow from the insufflator 26 to the cavity of the patient. The air from the insufflator 26 is conveyed through a conduit 113.

The charged trocar controller 115 may be electrically connected to the trocar 20 by means of a conduit 120. The electrical lines are connected to the plates 47 and 62 by metal strips 125, 130 extending inside the trocar 20.

In an alternate embodiment shown in FIG. 3, the electrical connection between the charged trocar controller 110 and the plates 4 7 and 62 in the electrostatic precipitator of the present invention is electrically connected to the flow meter 110 such that the ionizer/negative charge plate 47 is only charged when the insufflation gas is entering the patient as detected by the flow meter 110.

Figure 4:
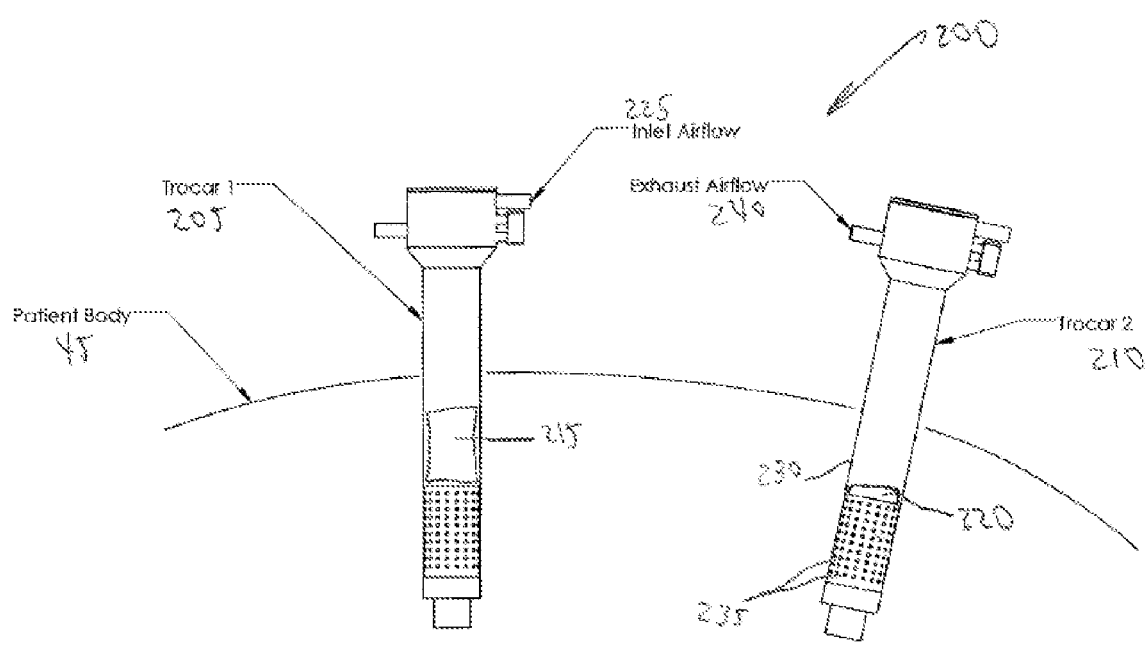
FIG. 4 is an alternative embodiment of a smoke collecting trocar system.

Turning to FIG. 4, in yet another embodiment of the invention, a system 200 may include two trocars 205 and 210. The first trocar 205 may include an ionizer/negative charge plate 215, and the second trocar 210 may include a positive charge collector plate 220. The first trocar 205 has an inlet port 225 for receiving insufflation gas which is conveyed across the ionizer/negative charge plate 215 to provide a negatively charged air stream entering the cavity.

The second trocar 210 has a outer surface 230 with a plurality of openings 235 for receiving negatively charged smoke particles from inside the cavity. The negatively charged smoke particles are attracted to the positive charge collector plate 220. The smoke particles leave the cavity and enter the second trocar 210 through openings 235 where the smoke particles become attached to the collector plate 220. The second trocar 210 may be provided with an exhaust airflow outlet 240 that may be connected to a vacuum source to provide for removal of some of the smoke by suction.

While the invention has been described in connection with a negative charge plate and a positive collection plate, it will be evident to persons of ordinary skill in the art based on this disclosure that the polarity of the plates may be reversed. Accordingly, the collection plate may be provided with a negative charge, and the charge plate may be provided with a positive charge. The components may be described as an electrically charged collection plate and an electrically charged plate having a polarity opposite to the polarity of the electrically charged collection plate.

The present invention contemplates that many changes and modifications may be made. Therefore, while the presently-preferred form of the smoke collecting trocar has been shown and described, and several modifications and alternatives discussed, persons skilled in this art will readily appreciate that various additional changes and modifications may be made without departing from the spirit of the invention, as defined and differentiated by the following claims.

The invention claimed is:

1. An apparatus for reducing surgical smoke, the apparatus comprising:

a trocar comprising a tubular hollow body circumscribing a cavity extending through a longitudinal axis of the trocar with a gasket at a first end and an exit port at a second end, the tubular hollow body comprising a first wall circumscribing the cavity and a concentrically spaced apart second wall circumscribing a channel defined by a gap between the first wall and the second wall, the cavity operable to allow a flow to pass from the gasket and out the exit port, the trocar comprising an electrical connection and an inlet fluidly connected to the cavity;

a first plate operable to maintain an electric charge, the first plate disposed within the cavity on an interior surface of the first wall, the first plate operable to electrically charge the flow;

a second plate operable to maintain an electric charge disposed in the channel between the first wall and the spaced apart second wall;

an insufflator operable to provide the flow of gas to the cavity;

a charged trocar controller operable to provide an electric charge to the first plate and the second plate; and a flow meter in fluid connection between the insufflator and the trocar, the flow meter operable to measure the flow of gas from the insufflator to the cavity, wherein the electrical connection is electrically connected to the first plate, the second plate, and the charged trocar controller, wherein the inlet is fluidly connected to the insufflator and the flow meter.

2. The apparatus according to claim 1, wherein the electric charge on the first plate is opposite the electric charge on the second plate.

3. The apparatus according to claim 1, wherein the spaced apart second wall comprises a plurality of perforations.

4. The apparatus according to claim 1, wherein the first plate is operable to negatively charge particles, and the second plate is operable to collect and attract negatively charged air particles.

5. The apparatus according to claim 1, the trocar further comprising an air inlet adjacent the first end fluidly coupled to the cavity operable to pass air through the air inlet through the cavity, and an electrical connection operably coupled to provide an electric charge to the first plate and the second plate.

6. The apparatus according to claim 1, the trocar further comprising an air exhaust port fluidly coupled to the cavity.

7. A method of removing gas, the method comprising:
(a) providing a trocar comprising a tubular hollow body circumscribing a cavity extending through a longitudinal axis of the trocar with a gasket at a first end and an exit port at a second end, the tubular hollow body comprising a first wall circumscribing the cavity and a concentrically spaced apart second wall circumscribing a channel defined by a gap between the first wall and the second wall, the cavity operable to allow a flow of gas to pass from the gasket and out the exit port, the tubular hollow body maintaining a first plate and a second plate, the first plate disposed within the cavity on an interior surface of the first wall, the first plate operable to maintain an electric charge the flow of gas, the second plate disposed in the channel, the second plate operable to maintain an opposite electric charge, an insufflator operable to provide the flow of gas to the cavity, a charged trocar controller operable to provide an electric charge to the first plate and the second plate, and a flow meter in fluid connection between the insufflator and the trocar, the flow meter operable to measure the flow of gas from the insufflator to the cavity, the trocar comprising an electrical connection and an inlet fluidly connected to the cavity, wherein the electrical connection is electrically connected to the first plate, the second plate, and the charged trocar controller, and wherein the inlet is fluidly connected to the insufflator and the flow meter;
(b) inserting the trocar into a surgical cavity; and
(c) electrically charging the first plate and the second plate by the charged trocar controller to ionize particles within the surgical cavity and attract the particles toward one of the first plate and the second plate.

8. The method according to claim 7, the method further comprising insufflating the surgical cavity with gas by the insufflator.

9. The method according to claim 7, the method further comprising removing gas from the surgical cavity by a vacuum fluidly coupled to the trocar.

10. The method according to claim 7, wherein the second plate comprises a plurality of perforations operable to collect charged particle.

11. The method according to claim 7, wherein the flow meter is electrically connected between the charged controller and the first plate and the second plate.

\* \* \* \* \*